(12) United States Patent
Jacoby

(10) Patent No.: US 11,540,899 B2
(45) Date of Patent: Jan. 3, 2023

(54) METHODS AND APPARATUS FOR PERIODONTAL SCALING AND DEBRIDEMENT AND GUM TISSUE ABLATION FOR TREATING PERIODONTAL AND PERI-IMPLANT DISEASE

(71) Applicant: Bennett H. Jacoby, Lihue, HI (US)

(72) Inventor: Bennett H. Jacoby, Lihue, HI (US)

(*) Notice: Subject to any disclaimer, the term of this patent is extended or adjusted under 35 U.S.C. 154(b) by 0 days.

(21) Appl. No.: 16/295,769

(22) Filed: Mar. 7, 2019

(65) Prior Publication Data
US 2019/0307529 A1 Oct. 10, 2019

Related U.S. Application Data

(60) Provisional application No. 62/652,459, filed on Apr. 4, 2018.

(51) Int. Cl.
*A61C 1/07* (2006.01)
*A61C 1/00* (2006.01)
(Continued)

(52) U.S. Cl.
CPC ............ *A61C 1/0046* (2013.01); *A61B 18/22* (2013.01); *A61C 17/20* (2013.01); *A61Q 11/02* (2013.01);
(Continued)

(58) Field of Classification Search
CPC .............. A61C 1/07; A61C 17/20; A61C 3/03
(Continued)

(56) References Cited

U.S. PATENT DOCUMENTS

| 749,624 A | * | 1/1904 | McCullough |
| 2,990,616 A | * | 7/1961 | Kuris ............. A61C 1/07 433/119 |

(Continued)

FOREIGN PATENT DOCUMENTS

| EP | 2719356 A1 | 4/2014 |
| FR | 2773468 A1 | 1/1998 |

(Continued)

OTHER PUBLICATIONS

United States Patent and Trademark Office, "International Search Report", dated May 23, 2019, International Application No. PCT/US2019/024396.

(Continued)

*Primary Examiner* — Ralph A Lewis
(74) *Attorney, Agent, or Firm* — Bretton L. Crockett; TechLaw Ventures, PLLC

(57) ABSTRACT

The present disclosure is directed to tools, systems and methods for recontouring/reshaping gum tissue by engaging a consumable tip on a powered tool to abrade/ablate excess or mal-contoured gum tissue to allow better visualization of the tooth/implant structure and reduce the periodontal pockets to provide improved access for cleaning by both the patient and clinician. In some embodiments, the powered tool may use vibrational movement, longitudinal reciprocating movement, rotational movement, reciprocating rotational movement, or a combination of any of the above movement schemes. In some embodiments, a consumable tip may be directed for cleaning tooth/implant surfaces and for recontouring/reshaping gum tissue. The powered tool itself may be constructed to allow the cooling water flow used for operation to be directed to the site where the procedure is carried out for irrigation or to be directed (Continued)

elsewhere at the user's selection to facilitate gum contouring procedures.

46 Claims, 8 Drawing Sheets

(51) Int. Cl.
*A61C 17/20* (2006.01)
*A61B 18/22* (2006.01)
*A61Q 11/02* (2006.01)
A61C 8/02 (2006.01)
A61B 18/00 (2006.01)
A61B 5/00 (2006.01)

(52) U.S. Cl.
CPC ... *A61B 5/0088* (2013.01); *A61B 2018/00321* (2013.01); *A61B 2018/00577* (2013.01); *A61C 8/0006* (2013.01)

(58) Field of Classification Search
USPC .......................................................... 433/165
See application file for complete search history.

(56) References Cited

U.S. PATENT DOCUMENTS

| | | | | |
|---|---|---|---|---|
| 3,645,255 A * | 2/1972 | Robinson | ................ | A61C 17/20 601/2 |
| 4,283,174 A * | 8/1981 | Sertich | ................... | A61C 17/20 433/119 |
| 4,365,957 A | 12/1982 | Das | | |
| 4,913,133 A * | 4/1990 | Tichy | ..................... | A61C 17/20 433/142 |
| 5,100,321 A * | 3/1992 | Coss | ........................ | A61C 3/03 433/118 |
| 5,188,531 A * | 2/1993 | Von Sutfin | ............... | A61C 3/03 433/118 |
| 5,205,817 A * | 4/1993 | Idemoto | ............... | A61C 8/0089 606/169 |
| 5,236,358 A * | 8/1993 | Sieffert | .................. | A61C 17/20 433/119 |
| 5,435,722 A * | 7/1995 | Mandell | ................. | A61C 1/052 433/165 |
| 5,577,911 A * | 11/1996 | Garfinkel | ................. | A61C 17/20 433/119 |
| 5,643,305 A | 7/1997 | Al-Tameem | | |
| 5,674,074 A * | 10/1997 | Angelo, Jr. | .......... | A61C 8/0006 433/215 |
| 5,816,808 A * | 10/1998 | Gambarini | ................ | A61C 3/03 433/166 |
| 5,899,693 A * | 5/1999 | Himeno | .................. | A61C 17/20 433/118 |
| 6,726,531 B1 * | 4/2004 | Harrel | ...................... | A61C 3/03 433/119 |
| 6,910,889 B1 * | 6/2005 | Hickok | .................... | A61C 3/03 433/102 |
| 9,248,004 B2 * | 2/2016 | Araya | ...................... | A61C 3/03 |
| D750,781 S | 3/2016 | Tanaka et al. | | |
| 11,207,084 B2 * | 12/2021 | Feng | ...................... | A61B 17/32 |
| 2003/0096213 A1 | 5/2003 | Hickok et al. | | |
| 2004/0023187 A1 * | 2/2004 | Hickok | .................... | A61C 3/03 433/119 |
| 2004/0191725 A1 * | 9/2004 | Szymaitis | ................ | A61C 3/02 433/165 |
| 2005/0244788 A1 | 11/2005 | Feine | | |
| 2009/0011383 A1 * | 1/2009 | Chen | ........................ | A61C 3/03 433/143 |
| 2011/0033817 A1 | 2/2011 | McKay | | |
| 2011/0033823 A1 * | 2/2011 | Gersh | .................... | A61C 17/20 433/119 |
| 2013/0337404 A1 * | 12/2013 | Feine | ..................... | A61C 3/025 433/86 |
| 2014/0106297 A1 * | 4/2014 | Schmidlin | ................ | A61C 3/02 433/82 |
| 2016/0081764 A1 | 3/2016 | Yasushi et al. | | |
| 2017/0333169 A1 * | 11/2017 | Hoang | ................ | A61C 17/005 |
| 2020/0022781 A1 | 1/2020 | Jacoby | | |

FOREIGN PATENT DOCUMENTS

| WO | 2017013680 A2 | 1/2017 |
|---|---|---|
| WO | 2019195059 A1 | 10/2019 |

OTHER PUBLICATIONS

FDA 510(k) application, "Diamond Coated Inserts," DENTSPLY International, Jan. 10, 2003, https://www.accessdata.fda.gov/cdrh_docs/pdf3/K030111.pdf.

FDA 510(k) application, "Piezosurgery Plus (Sonic Surgical Instrument And Accessories/Attachments)," Mectron Spa, May 25, 2016, https://www.accessdata.fda.gov/cdrh_docs/pdf15/K153743.pdf.

European Search Report and Written Opinion Received from PCT Application No. PCT/US2019024396, dated Oct. 13, 2021, 7 Pages.

* cited by examiner

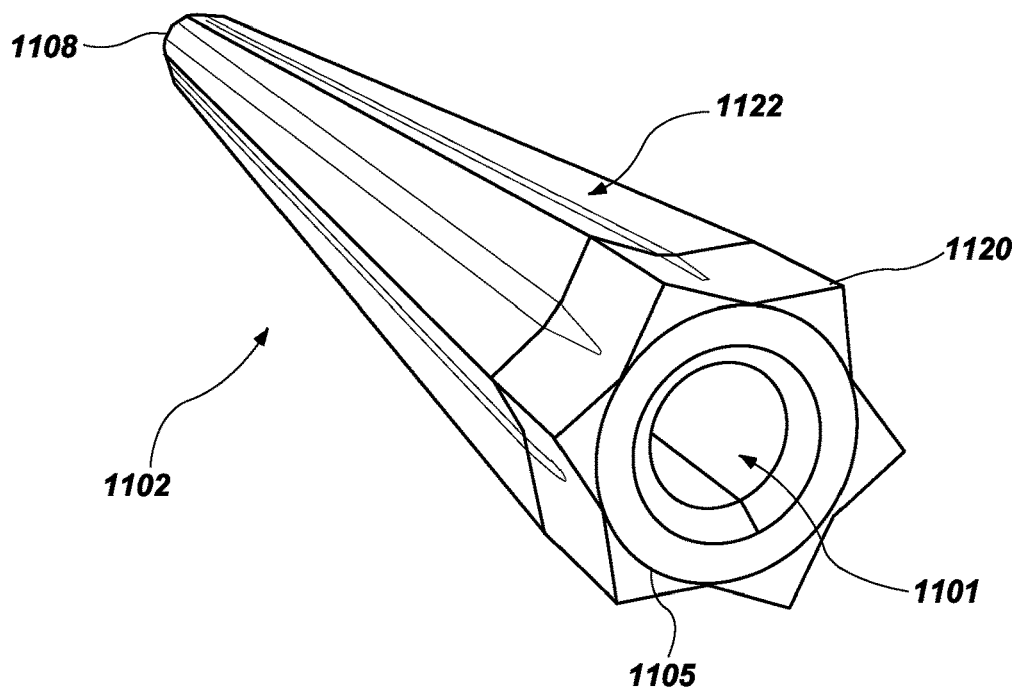
FIG. 11
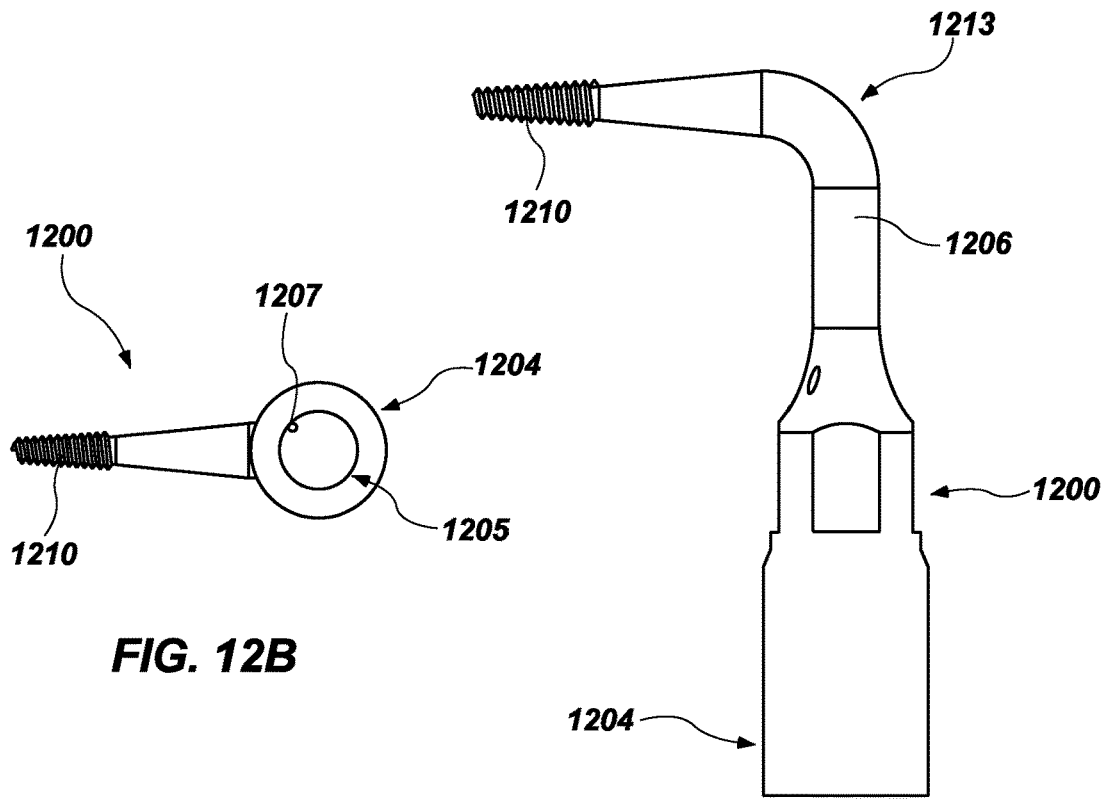
FIG. 12B
FIG. 12A

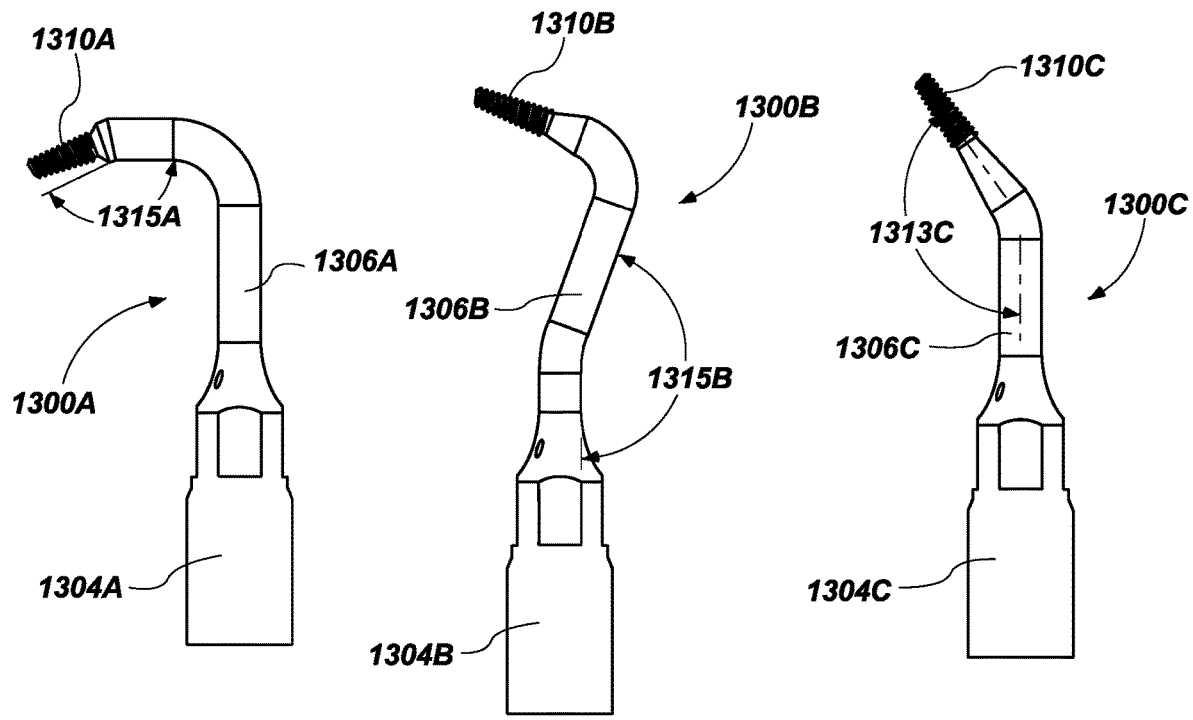
FIG. 13A  FIG. 13B  FIG. 13C
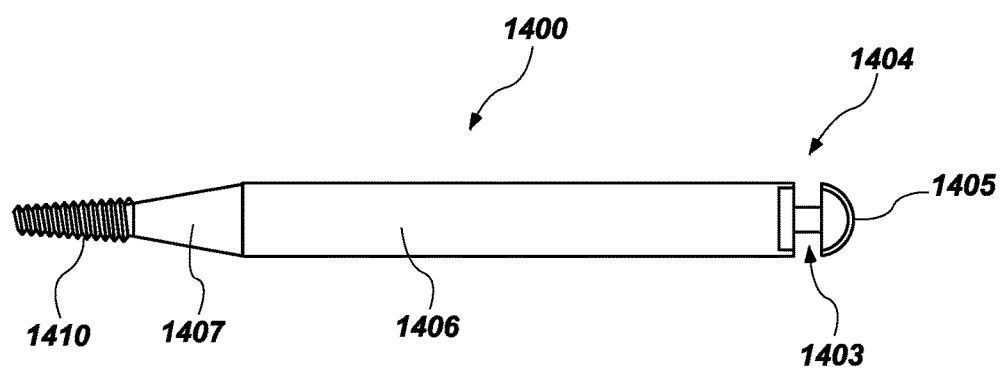
FIG. 14

METHODS AND APPARATUS FOR PERIODONTAL SCALING AND DEBRIDEMENT AND GUM TISSUE ABLATION FOR TREATING PERIODONTAL AND PERI-IMPLANT DISEASE

CROSS-REFERENCE TO RELATED APPLICATION

This application claims the benefit of U.S. Provisional Application No. 62/652,459, filed Apr. 4, 2018, which is hereby incorporated by reference herein in its entirety, including but not limited to those portions that specifically appear hereinafter.

TECHNICAL FIELD

The present disclosure relates to dental tools, systems and methods.

BACKGROUND

Periodontitis and peri-implantitis are some of the most common chronic diseases known to humanity. They are caused by various species of bacteria, viruses, their toxins and mineralized deposits (collectively hereon, "accretions") adherent to the tooth/implant surface above and below the gum line that cause inflammation, destroy the supporting structure of the tooth/implant and result in possible tooth/implant loss. As the supporting structures are destroyed, a "periodontal pocket" is created between the gum and the tooth/implant that needs to be addressed due to its propensity to lead to reinfection and to prevent patient and clinician access to all the accretions.

Current treatment regimens involve a first step of removing the accessible accretions with manual and powered tools. These tools are designed and configured to remove the soft and hard microbial accretions from around teeth or implants. This first step is often incompletely effective at removing enough of the accretions to eliminate the infection and inflammation due to the lack of visualization of the subgingival tooth/implant surfaces hidden within the periodontal pocket. In addition, periodontal pockets are a prime nidus for bacterial recolonization and reinfection post-treatment as clinical studies demonstrate that the ability for both patients and clinicians to effectively clean subgingival tooth/implant surfaces decreases with depth. Therefore, a second step of treatment is often indicated that involves removing the excess gum tissue with a scalpel or laser to reduce the pocket depth. This can allow the patient to completely debride the affected area on a daily basis to help prevent reinfection; and facilitate visualization of the subgingival tooth/implant structures by the clinician for more effective accretion removal both during the second phase of treatment and at subsequent periodic maintenance cleanings. This second step highlights the shortcoming of the first step of treatment: that it is often inadequate at both efficacy of accretion removal and pocket reduction while the second step is costly, time consuming and painful. Thus, an unmet need exists for a device or method that can affect a one-step: "pocket reduction", providing increased visualization, and highly effective accretion removal, all resulting in more definitive long-term resolution of the infection.

Currently known tools are not designed for such uses. Instead, many known powered scalers utilize smooth metal tips designed and configured to remove hard and soft accretions. These are highly ablative to tooth surface with minimal effect on the gingiva, so they would not be useful for gingival recontouring. Other tools such as piezo bone surgery units and dental drills use abrasive/contoured metal tips that are designed and configured to recontour teeth or bone, as well as remove extremely tenacious hard or soft accretions. These could be somewhat effective at recontouring the gingiva, but due to the tool design, hardness and abrasiveness, they would be prone to severely damage the tooth, implant or bone which is in close proximity to the gingiva during such use. Thus, these tools represent too high a risk to use for gingival recontouring or would have minimal effect on the gingiva. Similarly, plastic implant scalers designed for cleaning implants might be somewhat effective at recontouring gingiva but with such low efficiency as to be unusable for this purpose. In addition, they are not designed and configured to access all the necessary areas to recontour the gingiva appropriately. In addition, they are very inadequate at removing hard/soft accretions from tooth/implant structure due to their lack of surface features Accordingly, a powered scaler and rotary tool that was designed and configured to be safe for tooth/implant surfaces and highly effective at recontouring gingiva would be an improvement in the art. Such tools that are also ablative to accretions would be a further improvement in the art.

A minimally invasive system, device or method, using powered tools, designed and configured to effect both safe and effective gum ablation/recontouring to accomplish increased accretion visualization and removal, as well as pocket reduction, all without damaging the tooth, implant, ligament or bone would be a further improvement in the art.

SUMMARY

The present disclosure is directed to tools, systems and methods for recontouring/reshaping gum tissue (known as "gingivoplasty" and "gingivectomy" and curettage) by engaging a detachable and/or consumable tip on a powered tool to abrade/ablate excess or mal-contoured gum tissue to allow better visualization of the tooth/implant structure and reduce the periodontal pockets to provide improved access for cleaning by both the patient and clinician. The powered tool may use vibrational energy or movement (i.e. a sonic or ultrasonic scaler), longitudinal reciprocating movement, rotational movement, reciprocating rotational movement, or a combination of any of the above movement schemes.

In sonic embodiments, the consumable tip tools, systems and methods may be directed for cleaning tooth/implant surfaces by engaging the consumable tip with a tooth/implant surface to remove at least a portion of accretions from the tooth/implant surface without damaging the surface of the tooth/implant and simultaneously abrading/ablating excess or mal-contoured gum tissue to allow better visualization of the tooth/implant structure and reduce the periodontal pockets to provide improved access for cleaning by both the patient and clinician.

Tips and tools useful for such methods may include attached, detachable and/or consumable tips that are attached to a powered tool, such as an ultrasonic vibrational tool, a powered rotary tool such as a dental drill motor, or other powered tool, having an insert to which the tip may be attached. Such a tip may include an outer sheath that can be inserted into a periodontal pocket and, when energy is applied, will abrade or ablate the gum tissue from the inside out, similar to "gingival curettage" performed with a gracey curette, or the tip can be used from the outside in, similar to gingivectomy or gingivoplasty performed with a scalpel or laser. Such an outer sheath may be made from a suitable material to have a sharp or abrasive outer surface, such as a suitable contoured, particle filled, or textured plastic material. The outer sheath may be disposed on an inner core which reinforces and strengthens the outer sheath. In some embodiments, the inner core may extend past the distal end of the outer sheath and may be constructed of a suitable material, such as a metal, to contact the tooth, tooth root, or implant fixture surface and thereby effect debris removal like a typical powered tip. The powered tool itself may be constructed to allow the cooling water flow used for operation to be directed to the site where the procedure is carried out, for irrigation as is currently standard in these tools, or to be directed elsewhere at the user's selection to facilitate gum contouring procedures, as the irrigation lubricates the site which decreases the ablative ability of the tip.

The present disclosure further includes methods for treating periodontal pockets, including infrabony periodontal pockets, by recontouring the gum tissue to allow elimination of the pockets, and/or visualization and access into the pockets to allow treatment where pocket elimination cannot be achieved.

BRIEF DESCRIPTION OF THE DRAWINGS

Non-limiting and non-exhaustive implementations of the disclosure are described with reference to the following figures, wherein like reference numerals refer to like parts throughout the various views unless otherwise specified. It will be appreciated by those of ordinary skill in the art that the various drawings are for illustrative purposes only. The nature of the present disclosure, as well as other embodiments in accordance with this disclosure, may be more clearly understood by reference to the following detailed description, to the appended claims, and to the several drawings.

FIGS. 9, 10 and 11 each depict a rear perspective view of additional embodiments of powered tips useful in some embodiments in accordance with the present disclosure.

FIGS. 12A and 12B are bottom and side views, respectively, of an illustrative embodiment of an insert for utilizing detachable powered tips in accordance with the present disclosure with sonic or ultrasonic tools.

FIGS. 13A, 13B, and 13C are side views of three additional illustrative embodiments of inserts for utilizing detachable powered tips in accordance with the present disclosure with sonic or ultrasonic tools.

FIG. 14 is a side view of an illustrative embodiment of an adaptor for utilizing detachable powered tips in accordance with the present disclosure with a dental drill.

DETAILED DESCRIPTION

The present disclosure relates to apparatus, systems and methods for performing powered dental cleaning and periodontal pocket reduction in a single procedure. It will be appreciated by those skilled in the art that the embodiments herein described, while illustrative, are not intended to so limit this disclosure or the scope of the appended claims. Those skilled in the art will also understand that various combinations or modifications of the embodiments presented herein can be made without departing from the scope of this disclosure. All such alternate embodiments are within the scope of the present disclosure.

In a first aspect, methods, systems and apparatus in accordance with the present disclosure are directed to providing minimally invasive procedures that involve using the powered tools to effect both safe and effective gum ablation/recontouring as there is an unmet need for powered tools that are designed and configured to be highly effective at recontouring gingiva. Accordingly, the present disclosure includes powered tips that may feature ridged/textured/abrasive/high-friction zones for ablation of gum tissue.

The present disclosure further includes methods, systems and apparatus that are directed to providing minimally invasive procedures, preferably single-step procedures, that involve using the powered tools to effect both safe and effective gum ablation/recontouring and optional accretion removal as there is an unmet need for powered tools that are designed and configured to be safe for tooth or implant surfaces and highly effective at recontouring gingiva. In some versions, these tools may be ablative to accretions. Accordingly, the present disclosure includes powered tips that include both ridged/textured/abrasive/high-friction zones for ablation of gum tissue or recontouring gingiva and "safe zones" for contacting teeth without damaging them. Some illustrative tool tips may include one or more portions formed as a ridged/textured/abrasive/high-friction metal to ablate gum tissue and one or more portions formed as plastic safe zones to protect the teeth/implants (or mildly debride them of accretions). Other illustrative tips may include one or more portions that are ridged/textured/abrasive/high-friction plastic that contact gingiva and effectively recontours/ablates gingiva, and smooth metal "tartar zones" that contact tooth surfaces or implant fixture surfaces and will remove accretions from the those surfaces during gingival recontouring/ablation. Additional illustrative tips may include one or more portions that are ridged/textured/abrasive/high-friction plastic that effectively recontours/ablates gingiva, but that are safe for teeth/implants due to its low hardness as compared to the hardness of tooth/implant structure, or may have smooth "safe zones" that can safely come into contact with the teeth/implants such that it will not damage the tooth/implant structure.

Figure 1:
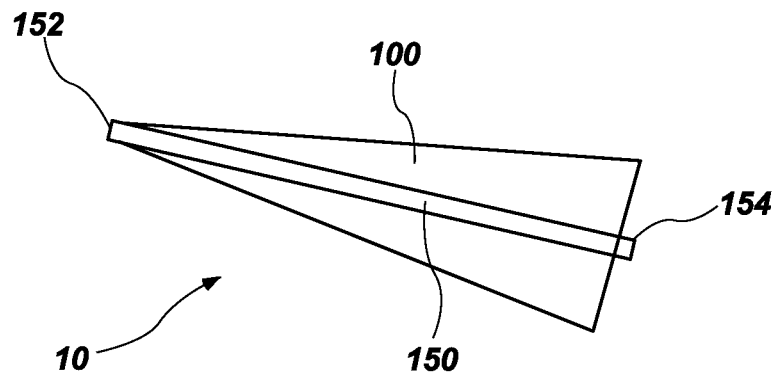
FIG. 1 depicts a first embodiment of a powered tip in accordance with the present disclosure.

Turning to FIG. 1, a schematic of a first scaler tip 10 for use in methods and procedures in accordance with the present disclosure is depicted. A metal core 150 has a distal end 152 that is exposed and a proximal end 154 that is configured for attachment to an ultrasonic/sonic/powered scaler insert tool, as by threading. A sheath 100 of an abrasive material, preferably a plastic material such as PEEK, that may be a high friction plastic and/or have a ridged, textured or abrasive surface is disposed on the core 150. As depicted, the sheath 100 may have a conical shape.

Figure 2:
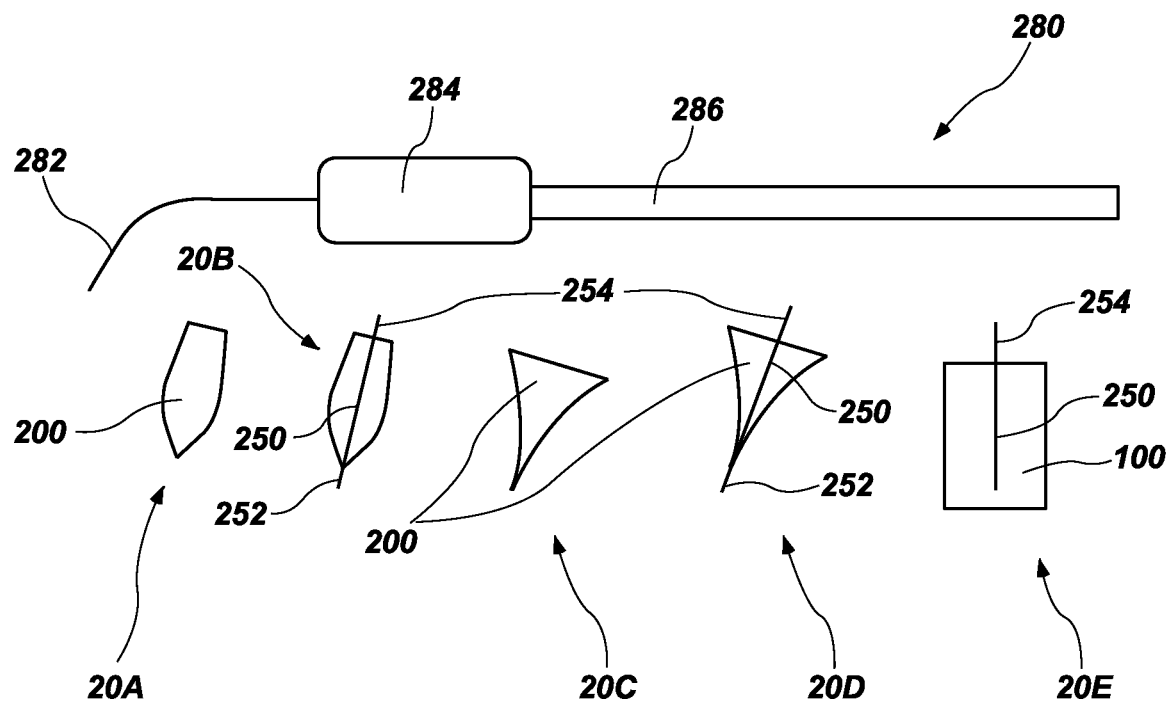
FIG. 2 depicts a set of five additional powered tip embodiments and an ultrasonic/sonic/powered tool for use in some embodiments in accordance with the present disclosure.

Turning to FIG. 2, multiple embodiments of tips 20A, 20B, 20C, 20D and 20E, in accordance with the present disclosure are depicted. As with the embodiment of FIG. 1, each of tips 20B, 20D and 20E, includes a sheath portion 200. It will be appreciated that tips 20A and 20C depict embodiments that do not contain core portions like that depicted in FIG. 1, or tips 20B, 20D or 20E. For such embodiments, the proximal end may include an attachment structure, such as a threaded bore, that will provide for the tip's attachment to a powered insert's distal end, such as 282, or this coreless sheath/tip may be permanently affixed, intended for single use, to the distal end of a powered insert such as 282.

Tips 20A, 20B 20C, 20D and 20E may be formed with an exposed outer surface of a material that has ridged, abrasive, and/or friction qualities. Further, tips 20A, 20B, 20C and 20D are sized and configured such that at least the distal portion, which may be curved towards a point, will fit between the gum and the tooth/implant, or between teeth and/or implants on a patient in which gum ablation or removal is indicated. The larger sizes, especially nearer the proximal portion, will significantly distend the gum tissue as the sheath/tip is inserted into a periodontal pocket. When a sheath/tip 200 is pressing up against the gum tissue and energy is supplied to a powered tool 280, in which the tip is mounted is active, the ridged/abrasive/friction quality of the sheath/tip 200 will abrade/degrade/ablate the gum tissue from the inside out, or outside in (from the epithelial surface inward toward the connective tissue.) In the depicted embodiment, it will be appreciated that the powered tool 280, may be an ultrasonic or sonic powered tool that uses vibrational energy. The abrading or ablating of the gum tissue from the inside out will promote post procedural healing with a decreased pocket depth and will also create a temporary gap between the gum and the tooth/implant that will allow the operator to see microbial deposits on the root/implant below the gum line allowing effective removal at the time of treatment.

By contrast, these tips 20A-E are also sized and configured to allow reshaping and abrasion/ablation of the gum tissue from the gingival surface toward the periodontal pocket and need not be inserted between the gum and the tooth/implant.

As depicted, each of tips 20B, 20D and 20E, include a tip core 250, as with tip 10 of FIG. 1 and tip core 150. As with tip core 150, tip core 250 may be constructed of a material that will not damage but can be used to clean a tooth or implant fixture surface, such as a metal material with the smooth surface. The tip core 250 may be sized and configured to have the sheath 200 mounted on it or over it. The sheath 200 may be bonded permanently to the tip core, or a sheath interior aspect and a tip core exterior aspect may be threaded to allow attachment of one to the other while allowing replacement of either component independent of the other. For threaded embodiments, a mechanical barrier or "stop" may be built into either component to place a limit on the extent of insertion of either component on/in the other.

As best depicted with tips 20B and 20D, the tip core 250 may have an exposed distal end 252, which extends beyond the distal end of the sheath 200 to allow the tip core to contact the tooth, tooth root, or implant fixture surface to effect debris removal just like a typical ultrasonic/sonic/powered tip.

It will be appreciated that where a subgingival implant fixture itself is exposed and may be infected or have accretions disposed thereon, that it can be debrided using the metal tip core. For example, where exposed due to bone loss (or simply not being placed deep enough in the bone) the implant fixture surface can become infected and needs to be thoroughly cleaned. The exposed metal tip core will not make this already rough/threaded surface more bacterially retentive since the implant fixture surface is already bacterially retentive as a surface conducive to bone growth is necessarily conducive to bacterial growth due to roughness. On the other hand, where an implant fixture is not infected and/or still fully covered with bone, and only the subgingival smooth implant abutment or subgingival smooth crown surface is infected or has accretions, then these smooth surfaces should not be contacted by metal, since the metal tip could likely make the smooth surface more conducive to bacterial retention by scratching it or damaging it in some other way. Such surfaces may instead be cleaned using the sheath, especially any smooth areas disposed thereon.

A powered insert 280 may include a magnetostrictive stack portion 286, a handle 284 and an insert tip 282. The insert tip 282 may be constructed of a suitable material and may be permanently attached to, or threaded for attachment to, the powered insert 280. In sonic embodiments, the insert tip 282 may be an integral part of a tip core 250 or may be removably attached to a tip core 250 or a tip 200 via a thread or other reversible attachment means.

In one illustrative embodiment, where the tool is an ultrasonic or sonic powered tool, an entire assembled tool assembly 280 with an attached tip 20A, 20B, 20C, 20D or 20E may be placed into communicative connection with an ultrasonic or sonic energy generator that has a foot activator for the energy and/or water. The commercially available Parkell ultrasonic units or Cavitron ultrasonic units are examples of units that may be used.

Water irrigation and ultrasonic energy may then be applied to cool and power the unit respectively. The water flow may be adjusted by the user to provide optimal cooling of the insert (which gets hot when energy is applied) while allowing optimal gum abrasion rate and optimal bacterial deposit removal effectiveness/rate. In one aspect, the selected tip 20A-E, including sheath/tip 200 which may include a tip core 250, are used to reshape the gum tissue as desired from the exterior of the pocket to attain more hygienic gingival contour and reduced pocket depth.

In another aspect, the distal end of the selected tip 20A-D is inserted between the gum and the tooth/implant to effect internal ablation/abrasion of the pocket lining, creating a visible gap between the gum and the tooth/implant allowing the clinician to visualize and remove bacterial deposits. The user may also use the tip core 250, when present, to effect bacterial debris removal on the root surface. It will be appreciated that tissue ablation may be conducted from both the interior and the exterior surfaces in a single session of treatment and using the same tool. The procedure may be performed in any order.

Where the procedure is being performed on an implant, rather than a natural tooth, the clinician may decide to use a version that does not have a tip core 150 or 250 that is exposed on the distal end of the sheath in order to protect the implant surface from potential damage.

It will be appreciated that these methods may include inserting the tool into the crevice between the gum and tooth/implant, with or without accretion removal from the tooth/implant surface, and to thereby "open up" the crevice for better visualization, by either distending the gingiva away from the tooth/implant and/or by removing the pocket lining that is obscuring the root/implant surface. This can often reduce the height of the gum tissue for pocket depth reduction. It may also include applying the ultrasonic/sonic/powered tip to the gingival crest and/or gingival margin in a "top-down" or "outside-in" manner, also with or without accretion removal from the tooth/implant surface, to reduce the height of the gum tissue for pocket reduction and/or to reshape the gum tissue for lesion removal and/or to reshape the gum tissue to make the contours more cleanable for patient and/or clinician.

It has been found that gingival ablation/recontouring utilizing the described apparatus, systems and methods is often more efficient when minimal to no water flow occurs over the work site. However, lack of water flow is not typical nor normally desirable with ultrasonic or sonic powered tools. Both magnetostrictive and piezo ultrasonic inserts get very hot along their entire length during use and water flow is typically used for cooling the units. This water is then exhausted into the surgical site to continuously rinse the operative site and further cool the tip.

Figure 3A:
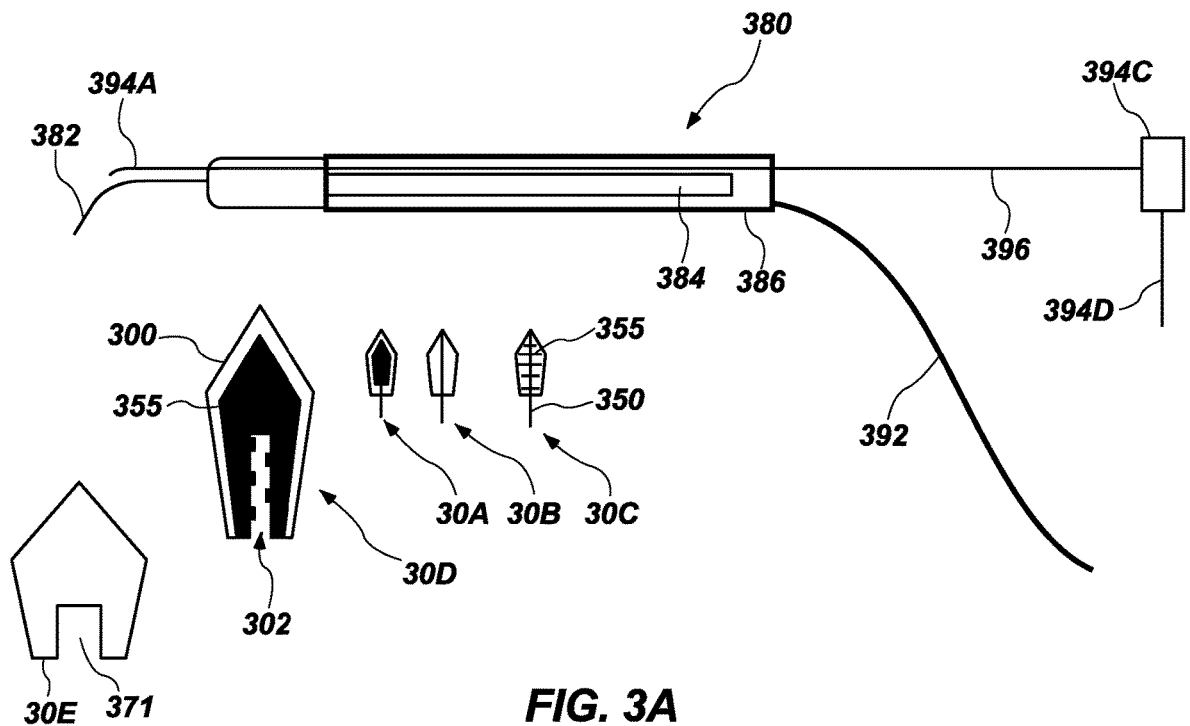
FIG. 3A depicts a set of some additional powered tip embodiments and another embodiment of an ultrasonic/sonic/powered tool for use in some embodiments in accordance with the present disclosure.

Turning to FIG. 3A another ultrasonic/sonic/powered tool assembly 380 for use in performing procedures in accordance with the present disclosure is depicted. Assembly 380 may be a magnetostrictive unit. In the depicted unit, water is introduced via cable 392 into tube 386 (which can serve as a handle) and bathes the magnetostrictive stack 384 with cooling water. In the depicted embodiment, this cooling water then exits tube 386 via a distal tube or pipe 394A directed towards the insert tip 382. Exiting water contacts the insert tip 382, and a tip, such as 30A, 30B, 30C or 30D disposed thereon. Thus, the water flow introduced through tube 392 is used for cooling the stack 384 and cooling, lubricating/flushing the operative site. During accretion removal, this is advantageous. However, during gingival ablation/recontouring, the flow through distal tube 394A may be redirected away from the operative site by opening a valve 394C and applying a vacuum to tubing 396 as from a vacuum source 394D.

Figure 3B:
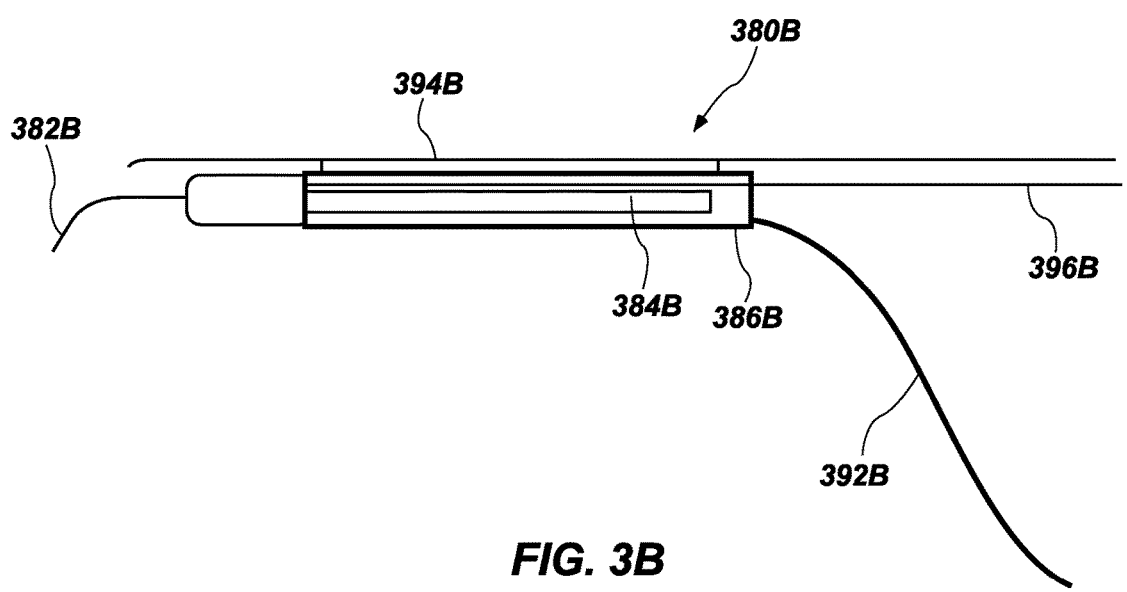
FIG. 3B depicts an alternative embodiment of an ultrasonic/sonic/powered tool for use in some embodiments in accordance with the present disclosure.

Another embodiment of an ultrasonic/sonic/powered tool assembly 380B for use in performing procedures in accordance with the present disclosure is depicted in FIG. 3B, which is similar to that of FIG. 3A, with the absence of distal tube or pipe 394A. Instead, all cooling water introduced through tube 392B exits the stack tube 386B in a direction away from the worksite. In the depicted embodiment, this may be through line 396B. If irrigation is desired at the operative site, it may be supplied through a separate pressurized water source, under operator control, such as a foot switch, through tube 394B which is directed towards the insert tip 382. Assemblies similar to that depicted in FIGS. 3A and 3B, thus allow cooling water flow to be directed at the discretion for the user towards or away from the work site. For example, a user could temporarily direct the water onto the worksite for quick flushing when needed or desired.

Additional scaler tips 30A, 30B, 30C, and 30D are depicted in FIG. 3A. These tips include a metal (or other rigid) supporting substructure 355 that is attached to the tip core 350. The sheath 300 of such tips may be attached to the supporting substructure using adhesive, or direct molding thereon. For example, directly molding a plastic sheath on a textured substructure surface to firmly bond the plastic to the metal. This can reinforce the tip and sheath for use. Tip 30D includes a threaded female hole 302 at the proximal end of the tip that can be screwed on to a threaded male at the distal end of the scaler insert at insert tip 382. In another tip embodiment tip 30E, no reinforcing substructure is built into the tip as the structural integrity of the tip is ensured by milling or molding from high modulus plastic such as PEEK. In this case, a threaded female hole 371 is included on the proximal end of the tip that can be screwed on to a threaded male at the distal end of the scaler insert at insert tip 382.

Figure 4A:
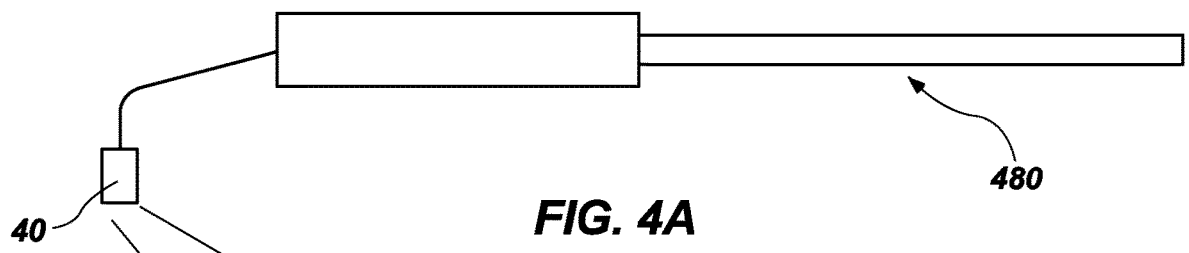
FIGS. 4A and 4B depict a mounted side and an end view of an additional embodiment of a powered tip with an "end abrading" conformation useful in some embodiments in accordance with the present disclosure.
Figure 4B:
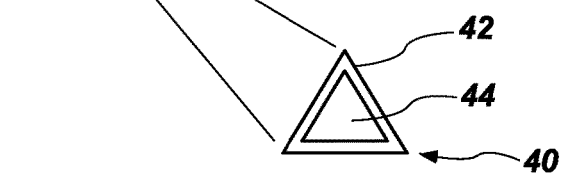

Turning to FIGS. 4A and 4B, another embodiment of a powered insert assembly 480 and a powered tip 40 is depicted. Tip 40 has sheath 42 that may be plastic which is abrasive on the end but is less abrasive or smooth on the sides so as to not damage a patient's tooth/implant surface. The sheath 42 surrounds a metal core 44 which is exposed at the end of the insert tip, but in a recess formed by the extending walls of the sheath 42. Core 44 has a textured exposed surface, or a diamond coated exposed surface that will abrade gum tissue, but which cannot come into contact with the teeth/implants due to the recess. The tip 40 may have a geometric shape, when viewed from the end, such as triangular or ovoid, and may be adjustable by turning at the end of the ultrasonic/sonic/powered tip as a user selects (for example, by friction fit with that requires strong hand force to turn) so as to allow for different orientations of the tip 40 with respect to a tooth/implant or gingival surface as may be advantageous for a particular use.

Figure 5B:
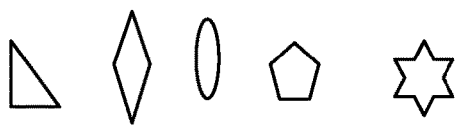
FIG. 5B depicts some cross-sectional profiles for powered tip conformations useful in some embodiments in accordance with the present disclosure.
Figure 5A:
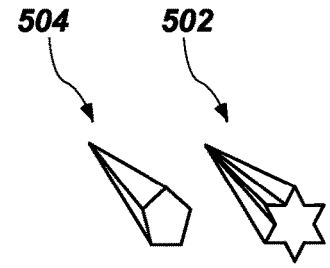
FIG. 5A depicts two additional profiles for powered tip conformations useful in some embodiments in accordance with the present disclosure.

FIG. 5A depicts two powered tips 502 and 504 with conformations useful in some embodiments in accordance with the present disclosure. Each powered tip 502 and 504 tapers from a wider base to a narrower distal end. Tip 504 has generally a pentagonal cross-sectional shape that forms corners and flat sides down the body of the tip. Tip 502 has a generally a "star"-shaped cross-sectional shape that forms corners and recessed areas down the body of the tip. Each tip may be constructed from an abrasive material, such as PEEK and may have a textured surface to increase gum ablation effectiveness. The different shapes and different designs may be useful for varying procedures or for use with different patients having different periodontal pocket shapes and issues to be addressed and may be selected by a practitioner as suitable for particular uses. In one illustrative embodiment, tip 502 may be about 0.4 inches in length from the tip to the base and the base may have a diameter of about 0.1 inches. It will be appreciated that these measurements are merely illustrative and other embodiments with different dimensions are possible and suitably sized tips for particular uses may be selected by a practitioner.

FIG. 5B depicts some cross-sectional profiles for ultrasonic/sonic/powered tip conformations useful in some embodiments in accordance with the present disclosure. These include shapes having sharp corners, rounded corners, flat planes and recesses on the sides of the tips. Such cross-sectional designs may be used on tapered tips for ablation from inside a periodontal pocket which may be performed in conjunction with the cleaning of the exposed tooth/implant root. Others may be tapered or non-tapered and used for ablation performed from outside a periodontal pocket. Each tip may be constructed from an abrasive material, such as PEEK or reinforced PEEK and may have a textured surface to increase gum ablation effectiveness. The different shapes and different designs may be useful for varying procedures or for use with different patients having different periodontal pocket shapes and issues to be addressed and may be selected by a practitioner as suitable for particular uses.

Figure 6A:
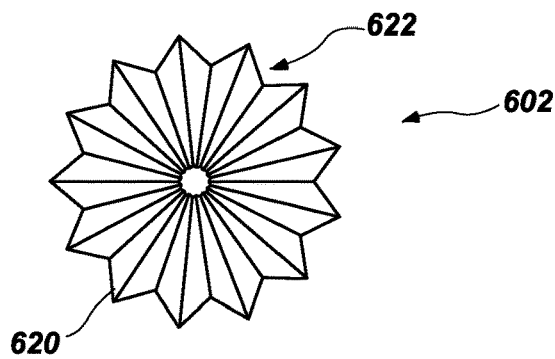
FIGS. 6A and 6B depict front end and side views of an additional embodiment of a powered tip useful in some embodiments in accordance with the present disclosure.
Figure 6B:
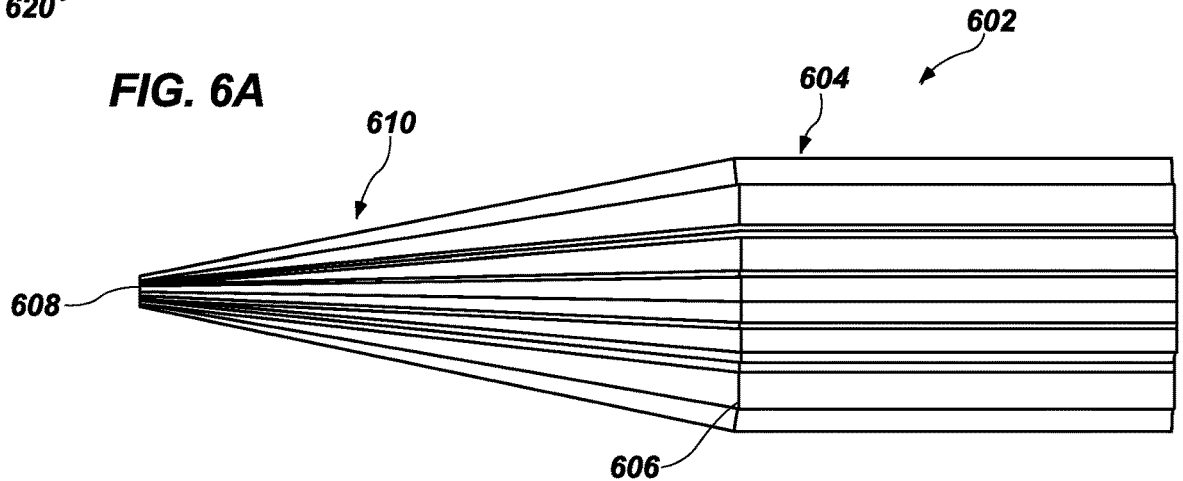

FIGS. 6A and 6B depict another powered tip 602 with a conformation useful in some embodiments in accordance with the present disclosure. Powered tip 602 may have a base portion 604 with a relatively constant cross-sectional diameter and a proximal tapering portion 610, beginning at a point 606, where the tip 602 tapers from the relatively wider base to a narrower distal end 608. Tip 604 has generally a "star shaped" cross-sectional defined by a number of ridges 620 and "valleys" 622 that form interior and exterior corners and flat surfaces therebetween down the body of the tip 602. Tip 602 tip may be constructed from an abrasive material, such as PEEK and may have a textured surface to increase gum ablation effectiveness. In one illustrative embodiment, tip 602 may be about 0.4 inches in length from the tip 608 to the base and the base may have a diameter of about 0.1 inches. It will be appreciated that these measurements are merely illustrative and other embodiments with different dimensions are possible and suitably sized tips for particular uses may be selected by a practitioner.

Figure 7A:
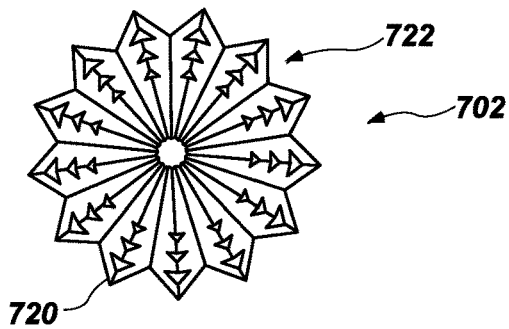
FIGS. 7A and 7B depict front end and side views of an additional embodiment of a powered tip useful in some embodiments in accordance with the present disclosure.
Figure 7B:
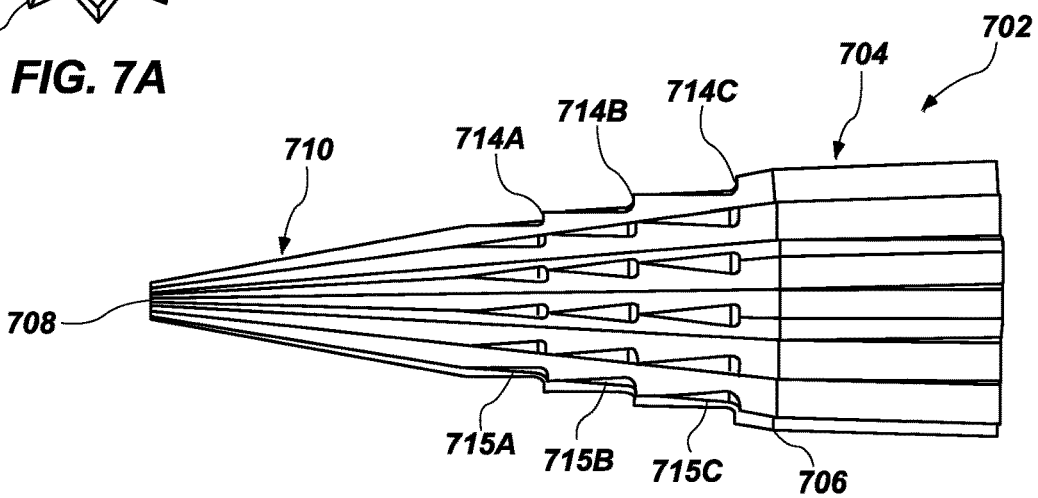

FIGS. 7A and 7B depict another powered tip 702 with a conformation useful in some embodiments in accordance with the present disclosure. Similar to tip 602, powered tip 702 may have a base portion 704 with a relatively constant cross-sectional diameter, or a relatively limited taper along its length, and a distal tapering portion 710, beginning at a point 706, where the tip 702 tapers from the relatively wider base to a narrower distal end 708. Tip 702 has generally a "star shaped" cross-sectional defined by a number of ridges 720 and "valleys" 722 that form interior and exterior corners and flat surfaces therebetween down the body of the tip 702.

Distal tapering portion 710 may include a series of generally horizontal portions 715A, 715B, 715C, separated by generally orthogonal vertical portions 714A, 714B, and 714C. These structures may be formed in the ridges 720, form generally planar rings around the circumference of the tip 702.

Tip 702 tip may be constructed from an abrasive material, such as PEEK and may have a textured surface to increase gum ablation effectiveness. In one illustrative embodiment, tip 702 may be about 0.4 inches in length from the tip 708 to the base and the base may have a diameter of about 0.1 inches. It will be appreciated that these measurements are merely illustrative and other embodiments with different dimensions are possible and suitably sized tips for particular uses may be selected by a practitioner.

Figure 8:
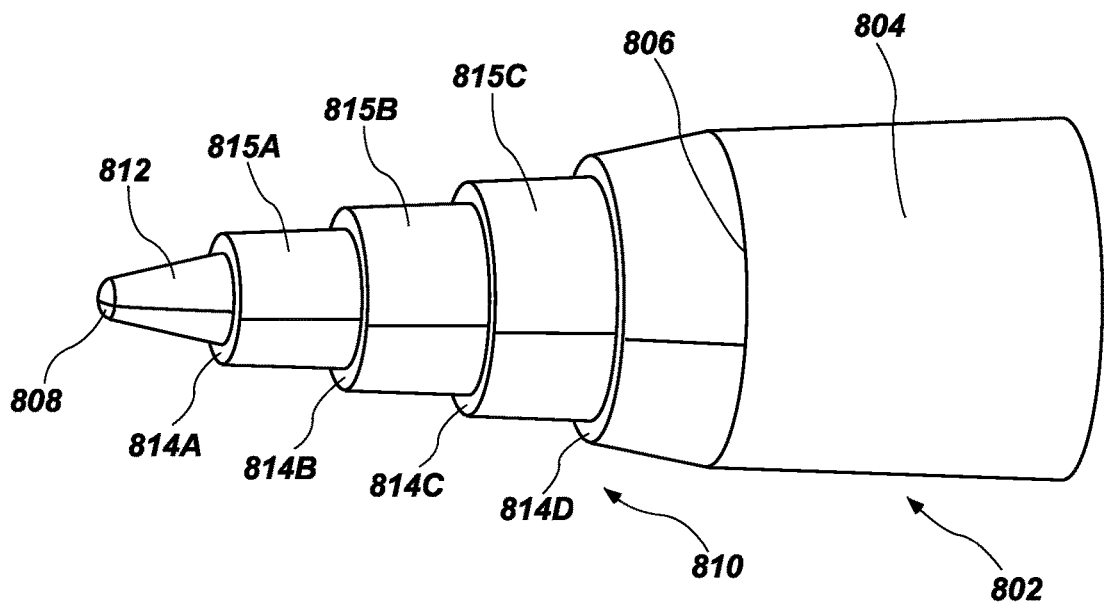
FIG. 8 depicts a side view of an additional embodiment of a powered tip useful in some embodiments in accordance with the present disclosure.

FIG. 8 depicts another powered tip 802 with a conformation useful in some embodiments in accordance with the present disclosure. Similar to tips 602 and 702, powered tip 802 may have a base portion 804 with a relatively constant cross-sectional diameter, or a relatively limited taper along its length, and a distal tapering portion 810, beginning at a point 806, where the tip 802 tapers from the relatively wider base to a narrower distal end 808. As depicted, tip 802 may have a generally round cross-sectional shape.

Distal tapering portion 810 may include a first tapered portion 812 from end 808 to a first generally orthogonal vertical portion 814, then a series of generally horizontal portions 815A, 815B, 815C, separated by generally orthogonal vertical portions 814B, 814C, and 814D, to form generally planar rings around the circumference of the tip 802.

Tip 802 tip may be constructed from an abrasive material, such as PEEK and may have a textured surface to increase gum ablation effectiveness. In one illustrative embodiment, tip 802 may be about 0.4 inches in length from the tip 808 to the base and the base may have a diameter of about 0.1 inches. It will be appreciated that these measurements are merely illustrative and other embodiments with different dimensions are possible and suitably sized tips for particular uses may be selected by a practitioner for particular uses.

Figure 9:
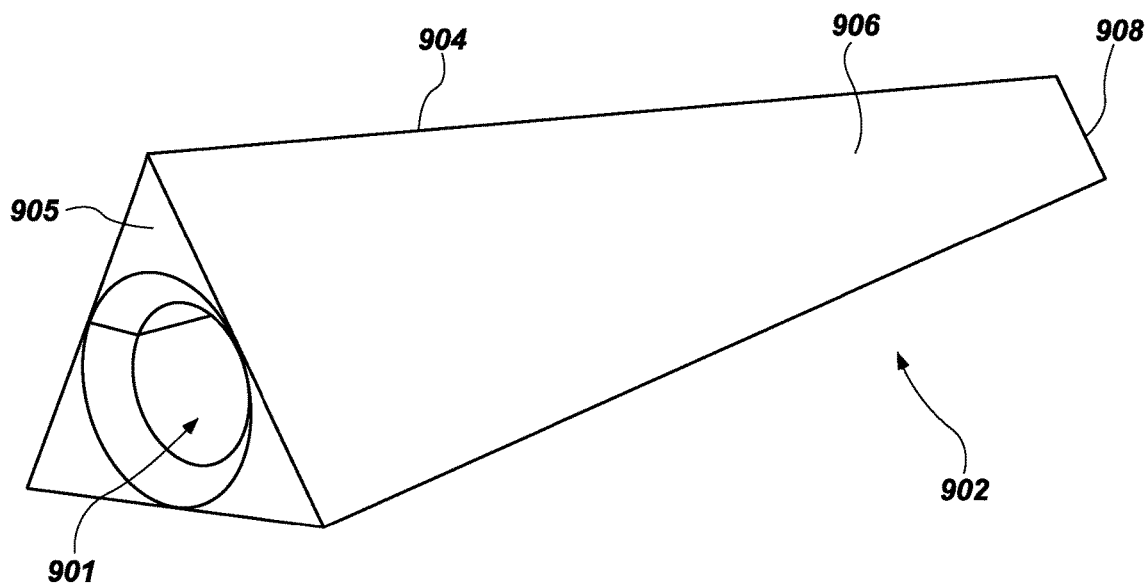

Turning to FIG. 9, another powered tip 902 with a conformation useful in some embodiments in accordance with the present disclosure is depicted. Powered tip 902 may have a base 905 with an opening therein to a bore 901 allowing connection to a powered tool, as by insertion of a shaft or an adaptor therein to connect the tip 902 to the tool. The body of the tip 902 extends from the base 905 to distal end 908. Along its length, the tip 902 may have a relatively constant cross-sectional diameter or may taper along its length to a relatively smaller distal end 908.

Tip 902 may have a geometric shape, when viewed from the end, such as triangular, formed by apexes 904 and extending side surfaces 906 therebetween. Tip 902 may be adjustable by turning at the end of the powered tool connection as a user selects (for example, by friction fit with that requires strong hand force to turn) so as to allow for different orientations of the tip 902 with respect to a tooth/implant or gingival surface as may be advantageous for a particular use.

Tip 902 tip may be constructed from an abrasive material, such as PEEK and may have a textured surface to increase gum ablation effectiveness. In one illustrative embodiment, tip 902 may be about 0.4 inches in length from the tip 908 to the base 905 and the base 905 may have a diameter of about 0.1 inches. It will be appreciated that these measurements are merely illustrative and other embodiments with different dimensions are possible and suitably sized tips for particular uses may be selected by a practitioner for particular uses.

Figure 10:
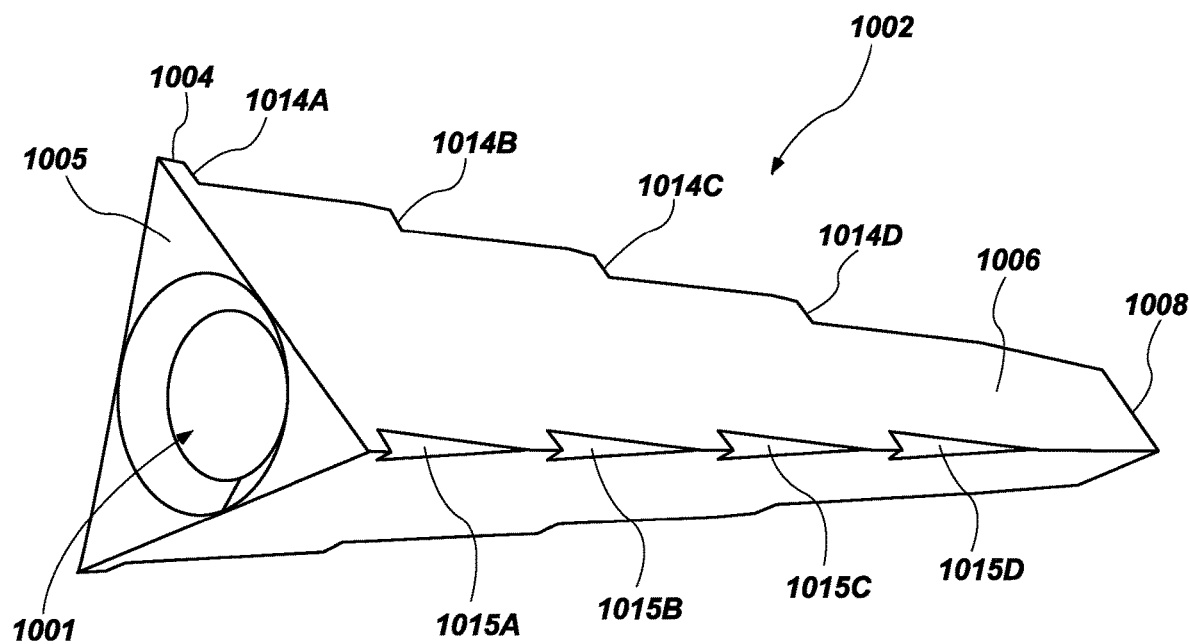

Turning to FIG. 10, another powered tip 1002 with a conformation useful in some embodiments in accordance with the present disclosure is depicted. Powered tip 1002 may have a base 1005 with an opening therein to a bore 1001 allowing connection to a powered tool, as by insertion of a shaft or an adaptor therein to connect the tip 1002 to the tool. The body of the tip 1002 extends from the base 1005 to distal end 1008. Along its length, the tip 1002 may have a relatively constant cross-sectional diameter or may taper along its length to a relatively smaller distal end 1008.

Tip 1002 may have a geometric shape, when viewed from the end, such as triangular, formed by apexes 1004 and extending side surfaces 1006 therebetween.

The apexes 1004 may include a series of generally horizontal portions 1015A, 1015B, 1015C, and 1015D separated by generally orthogonal vertical portions 1014A, 1014B, 1015C, and 1014C. As with rings and horizontal and vertical portions on tips 702 and 802, these structures formed in the ridges or apexes may provide cutting or roughened edges to enhance cleaning or ablation during use.

Tip 1002 may be adjustable by turning at the end of the powered tool connection as a user selects (for example, by friction fit with that requires strong hand force to turn) so as to allow for different orientations of the tip 1002 with respect to a tooth/implant or gingival surface as may be advantageous for a particular use.

Tip 1002 tip may be constructed from an abrasive material, such as PEEK and may have a textured surface to increase gum ablation effectiveness. In one illustrative embodiment, tip 1002 may be about 0.4 inches in length front the tip 1008 to the base 1005 and the base 1005 may have a diameter of about 0.1 inches. It will be appreciated that these measurements are merely illustrative and other embodiments with different dimensions are possible and suitably sized tips for particular uses may be selected by a practitioner for particular uses.

FIG. 11 depicts another powered tip 1102 with a conformation useful in some embodiments in accordance with the present disclosure. As depicted, powered tip 1102 may taper along its length, from base 1105 to a distal end 1108, similar to tips 502 and 504, discussed previously herein. Tip 1102 has generally a "star shaped" cross-sectional defined by a number of ridges 1120 and "valleys" 1122 that form interior and exterior corners and flat surfaces therebetween down the body of the tip 1102. The ridges and valleys may be more pronounced proximally as compared to the distal end in a gradual manner.

Tip 1102 tip may be constructed from an abrasive material, such as PEEK and may have a textured surface to increase gum ablation effectiveness. In one illustrative embodiment, tip 1102 may be about 0.4 inches in length from the tip 1108 to the base and the base may have a diameter of about 0.1 inches. It will be appreciated that these measurements are merely illustrative and other embodiments with different dimensions are possible and suitably sized tips for particular uses may be selected by a practitioner.

FIGS. 12A and 12B are bottom and side views, respectively, of an illustrative embodiment of an insert 1200 for utilizing detachable powered tips in accordance with the present disclosure with sonic or ultrasonic tools and are typically used with piezoelectric units instead of magnetostrictive units. At a first or proximal end, a tool attachment portion 1204 for connection to a sonic or ultrasonic powered dental hand tool is disposed. Connection structures to allow connection are accessible in the tool attachment portion, such as a thread. In the depicted embodiment, the connection structures include a socket 1205 formed as a bore into which a counterpart structure on the powered tool may be inserted and a locking structure, such as tab 1207 that may be rotated into a counterpart recess on the tool to retain the insert thereon.

A shaft 1206 extends distally from the tool attachment portion to a tip attachment portion 1210. As depicted, the shaft may narrow prior to the tip attachment portion. The tip attachment portion may be positioned at the distal end of the shaft 1206 and may include structures to allow for the detachable securing of a detachable tip, similar to those discussed elsewhere in this disclosure, thereon. In the depicted embodiment, the tip attachment portion 1210 may be threaded to allow the counterpart threads in the bore of a detachable tip to be threaded thereon for use. In another embodiment, the bore of the tip may be unthreaded, and on first attachment, the tip attachment portion 1210 "self taps" a thread into its counterpart bore of a detachable tip. In the embodiment depicted in FIGS. 12A and 12B, the shaft 1206 contains a single bend 1213 at a point along its length. In the depicted embodiment, the bend 1213 is generally at a 90 degree angle, such that the tip attachment portion 1210 extends generally orthogonal to the axis of the tool attachment portion 1204 and the proximal portion of the shaft 1206. It will be appreciated that the insert 1200, including shaft 1206 and tip attachment portion 1210 may be sized for use in a patient's mouth to allow for use therein in connection as discussed elsewhere herein. The insert may be constructed from a suitable material for the transmission of vibrations from the tool to the tip. In some embodiments, it may be formed as a unitary member by casting, milling, a combination thereof, or by other suitable techniques.

FIGS. 13A, 13B, and 13C are side views of three additional illustrative embodiments of inserts 1300A, 1300B, and 1300C for utilizing detachable powered tips in accordance with the present disclosure with sonic or ultrasonic tools. These are similar to the insert 1200 of FIGS. 12A and 12B, differing in the angling of the respective tip attachment portions 1310A, 1310B, and 1310C to the respective tool attachment portions 1304A, 1304B, and 1304C and are typically used with piezoelectric units instead of magnetostrictive units The shaft 1306A of insert 1300A is similar to that of insert 1200, with a second bend 1315A disposed at the base of the tip attachment portion 1310A, such that the tip attachment portion 1310A angles towards the tool connection portion 1304A. In the depicted embodiment, an axis of the tip attachment portion 1310A may be angle at about 160 degrees to an axis of the tip attachment portion 1304A.

The shaft 1306B of insert 1300B is similar to that of insert 1200, with a second bend 1315B disposed in the proximal portion of the shaft 1306A between the tool attachment portion 1304B and the first bend 1313B, such that the tip attachment portion 1310B angles away from the tool connection portion 1304B. In the depicted embodiment, second bend 1315B may be at angle of about 160 degrees to an axis of the tip attachment portion 1304B.

The shaft 1306C of insert 1300C is similar to that of insert 1200, except that the first bend 1313C angles the tip attachment portion 1310C angles away from the tool connection portion 1304B. In the depicted embodiment, first bend 1313C may be at angle of about 137 degrees to an axis of the tip attachment portion 1304B.

It will be appreciated that the different inserts 1200, 1300A, 1300B and 1300C have shafts that are of appropriate size and length and are angled for the advantageous positioning of the respective tip attachment portions 1210, 1310A, 1310B, and 1310C, for use in cleaning and debriding teeth and dental implants and/or performing the gingival curettage for subgingival visualization, gingivoplasty, gingivectomy and pocket reduction discussed herein. It will be appreciated that other inserts having varying angles or sizes for use in different applications and with different patients are within the scope of the present disclosure. Additionally, inserts intended for a single use that have a tip in accordance with the present disclosure permanently attached thereto.

Turning to FIG. 14, a side view of an illustrative embodiment of an adaptor 1400 for utilizing detachable powered tips in accordance with the present disclosure with a dental drill is depicted. At a first or proximal end, a tool attachment portion 1404 for connection to a dental drill or other rotary dental tool is disposed. Connection structures to allow connection are accessible in the tool attachment portion. In the depicted embodiment, the connection structures include a rounded proximal end 1405 to facilitate insertion into a dental drill, and an inset or groove 1403 for securing in the chuck of the latch-type tool to retain the insert thereon. Tool attachment 1404 may also be designed with straight parallel sides that are designed and configured to fit and be retained in what is commonly known in dentistry as a "FG" or "Friction Grip" type attachment mechanism within dental drill heads.

Shaft 1406 extends distally from the proximal end 1405 to a tip attachment portion 1410. As depicted, the shaft may narrow prior to the tip attachment portion 1410. The tip attachment portion 1410 may include structures to allow for the detachable securing of a detachable tip, similar to those discussed elsewhere in this disclosure, thereon. In the depicted embodiment, the tip attachment portion 1410 is threaded to allow the counterpart threads in the bore of a detachable tip to be threaded thereon for use. It will be appreciated that other inserts intended for a single use that have a tip in accordance with the present disclosure permanently attached thereto are also contemplated. The insert 1400 may be constructed from a suitable material for the use in a rotary dental tool. In the illustrative embodiment it may be formed as a unitary member by casting, milling, a combination thereof, or by other suitable techniques.

Figure 15:
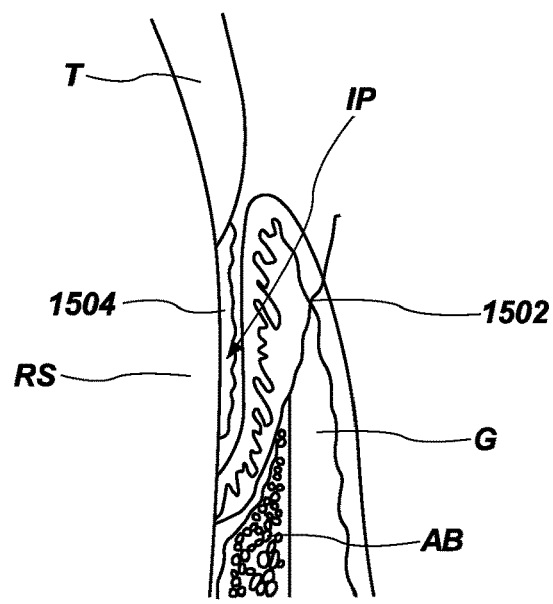
FIG. 15 illustrates an infrabony periodontal pocket and a method of improved treatment for this condition using powered tips in accordance with the present disclosure.

FIG. 15 illustrates an infrabony periodontal pocket and a method of improved treatment for this condition using powered tips in accordance with the present disclosure. As depicted, an infrabony periodontal pocket is a periodontal pocket in which the bottom is apical to the level of the adjacent alveolar bone. With some other types of periodontal pockets, simple excision of soft tissue can be performed to achieve pocket elimination. For example, a suprabony periodontal pocket has a bottom that is coronal to the alveolar bone and a horizontal cut can be performed to result in pocket elimination. This is not possible with infrabony pockets (also known as intrabony periodontal pockets), as it is not possible to cut to the level of the bone. Thus, even where a horizontal cut is performed at the lowest level possible, a pocket remains.

As depicted in FIG. 15, tools and tips in accordance with the present disclosure can be used to perform a "soft tissue curettage" of an infrabony periodontal pocket, such as that depicted, in order to open it up for visualization and treatment. The soft tissue above the line 1502 is ablated so that the entire root surface RS can be visualized for debridement of accretions 1504.

A practitioner may insert the distal end of a tip in accordance with the present disclosure into the infrabony pocket IP between the gum G and the root surface RS to effect internal ablation of the pocket lining, removing the tissue to create a visible gap between the gum G and the root surface RS that allows the clinician to visualize and remove accretions therein, including microbial deposits. The gum G tissue may be ablated to a line 1502 that tracks the curve of the alveolar bone AB. The practitioner may also use the tip to effect debris removal on the root surface RS.

It will be appreciated that these methods may include applying the ultrasonic/sonic/powered tip using vibrational movement, longitudinal reciprocating movement, rotational movement, reciprocating rotational movement, or a combination of any of these movements. For example, depending on the tip selected, a sonic or ultrasonic tool could be used or a rotationally enabled tip on a suitable adapter that is placed on a standard dental drill may be used.

Additionally, as discussed previously herein, it has been found that gingival recontouring is often more efficient when minimal to no water flow occurs over the work site. However, lack of water flow is not typical nor normally desirable within the ultrasonic or sonic powered tool's internal mechanisms. Both magnetostrictive and piezo ultrasonic inserts get very hot along their entire length within the handpiece during use and thus, internal water flow is required to cool the internal mechanisms which is then commonly vented onto the work site. Accordingly, in the present application, the practitioner may direct water flow away from, or towards, the work site as the procedure is performed, as discussed previously herein to enhance performance, while providing cleansing flow to the work site only as needed b the clinician.

In some embodiments, the methods may include the modification of the tip by the practitioner prior to, or during, use to alter the surface texture thereon to enhance the use of the tip for ablation or accretion removal. In one illustrative example, a tip, similar to one of those depicted as tip 504 or tip 802 and discussed previously herein, that uses a basic geometrically cross-sectional shape with planar surfaces is used. The tip may be formed of a plastic material with high friction properties, such as PEEK or reinforced PEEK. Where appropriate, the practitioner may decide to change the surface texture on the tip to improve a desired performance characteristic during use, for example to enhance ablation of soft tissue in periodontal recontouring.

Figure 16:
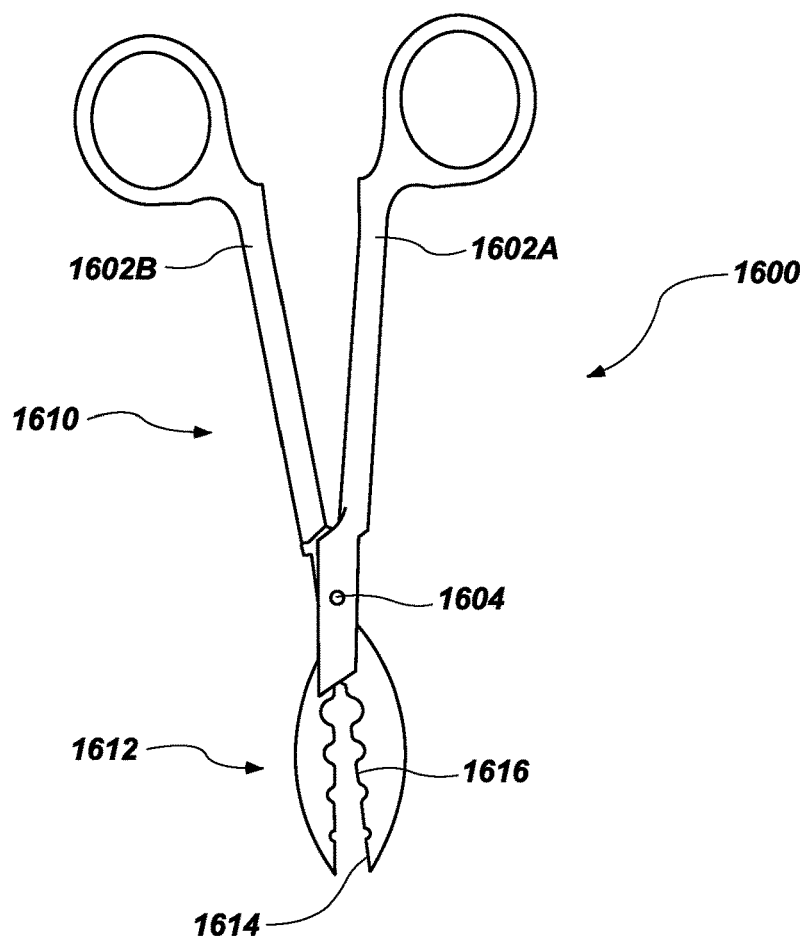
FIG. 16 is a side view of one illustrative embodiment of a clamp for imparting texture to a powered tip in accordance with one aspect of the present disclosure.

A separate tool may then be used, to clamp the tip therein and impart a surface texture on the on the tip surface. For example, a clamp 1600 similar to that depicted in FIG. 16 may be used. Clamp 1600 may have be formed similar to a hemostat or a surgical clamp, of two members 1602A and 1602B connected to each other at a rotation point 1604, to define an actuating handle portion 1610 and a clamping portion 1612 formed with two counterpart clamping members, each having an internal surface 1614 that included a desired texture impression 1616 formed thereon and is designed to correspond to at least a portion of a tip in accordance with the present disclosure. The desired casting impression may be formed to create ridges and planes on a tip when actuated thereon. A practitioner may simply clamp the tip in the clamping portion 1612 and actuate the actuating handle portion 1610 to compress the tip therein and impart a desired surface texture on the on the tip surface.

It will be appreciated that in addition to that depicted, other clamps that can impart a desired texture may be used. In one example, a ridged hemostat may be compressed on a tip constructed from the PEEK material to impart a surface texture thereon.

Further, although specific implementations of the disclosure have been described and illustrated, the disclosure is not to be limited to the specific forms or arrangements of parts so described and illustrated. The scope of the disclosure is to be defined by the claims appended hereto, any future claims submitted here and in different applications, and their equivalents.

What is claimed is:

1. A tip for use in removing gum tissue with a powered dental tool, comprising:
    an elongated member having a proximal end and a distal end;
    a tool attachment structure for mounting to a tip mounting structure accessible at the proximal end, such that upon mounting to a powered tool the tip may be actuated by the application of energy through the powered tool; and
    at least one gum tissue removal portion on the outer surface of the tip that when brought in contact with a patient's gum tissue and actuated will remove gum tissue, and comprising a plurality of portions defined by generally flat surfaces extending parallel to an axis defined by the proximal end to distal end direction of the tip to define a plurality of generally flat ring-shaped portions and a plurality of generally planar portions extending in a direction orthogonal to the axis defined by the proximal end to distal end direction of the tip, with at least two of the generally planar portions separated by portions defined by generally flat surfaces to define contiguous sections of the outer surface of the tip.

2. The tip of claim 1, wherein the tool attachment structure for mounting to the tip mounting structure comprises a bore in the tip that is accessible through an opening at the proximal end.

3. The tip of claim 1, wherein the tip has a generally round cross-sectional shape.

4. The tip of claim 3, further comprising a first tapered portion extending from the distal end of the tip to the plurality of generally flat ring shaped portions.

5. A method of removing gum tissue to allow better visualization and surface cleaning, the method comprising:
mounting a tip on a powered dental tool, the tip formed as an elongated member having a proximal end and a distal end, the tip further comprising at least one gum tissue removal portion on the outer surface of the tip comprising a portion including features that remove gum tissue upon activation;
contacting the mounted tip against a patient's gum tissue to be removed; and
actuating the powered dental tool to remove the patient's gum tissue at a point of contact with the mounted tip, wherein removing gum tissue comprises removing at least a portion of the patient's gingival crest; and
effecting powered debris removal of accretions from a surface of a tooth or a dental implant with the tip during the same procedure as the gum tissue removal by contacting the surface with the tip.

6. The method of claim 5, further comprising redirecting at least a portion of water flow for cooling the powered dental tool to exit the powered dental tool at a location away from the mounted tip thereby increasing gum tissue removal efficiency when directed by a practitioner operating the powered dental tool.

7. The method of claim 5, wherein effecting powered debris removal of accretions from a tooth surface comprises effecting powered debris removal of microbial deposits from a tooth surface with the tip.

8. The method of claim 7, wherein contacting the tooth surface with the tip comprises contacting the tooth surface with a portion of the tip constructed from a material having a hardness that is less than the hardness of the tooth surface.

9. The method of claim 5, wherein the tip has a triangular cross-sectional shape.

10. The method of claim 5, wherein the tip tapers towards the distal end.

11. The method of claim 10, wherein the tip includes a plurality of ridges converging towards the distal point.

12. The method according to claim 5, wherein actuating the powered dental tool comprises actuating the powered dental tool to impart energy in the form of vibrational movement, longitudinal reciprocating movement, rotational movement, reciprocating rotational movement, or a combination of the above movement schemes to the mounted tip.

13. A method of removing gum tissue to reduce periodontal or peri-implant pockets, the method comprising:
mounting a tip on a powered dental tool, the tip formed as an elongated member having a proximal end and a distal end, the tip further comprising at least one gum tissue removal portion on the outer surface of the tip comprising a portion including features that remove gum tissue upon activation;
contacting the mounted tip against a patient's gum tissue to be removed comprising inserting the distal end of the mounted tip into a periodontal pocket and actuating the powered dental tool with the mounted tip to remove the gum tissue including at least a portion of the patient's gingival crest, and adjacent marginal gingiva to reduce the depth of the periodontal pocket to create a visible gap between the patient's gum tissue and a tooth surface or a dental implant surface that improved visual access for a clinician to visualize subgingival structures for diagnosis or treatment.

14. The method of claim 13, further comprising contacting the tooth surface or dental implant surface with the tip to thereby remove accretions therefrom during the same procedure as the gum tissue removal.

15. The method of claim 14, wherein contacting the tooth surface with the tip comprises contacting the tooth surface with a portion of the tip constructed from a material having a hardness that is less than the hardness of the tooth surface.

16. The method of claim 13, further comprising redirecting at least a portion of water flow for cooling the powered dental tool from exiting the powered dental tool directed to the mounted tip to flush the operative site to exiting at another location away from the mounted tip and away from the operative site at the actuation of a valve as directed by a practitioner operating the powered dental tool.

17. The method of claim 13, wherein the tip has a triangular cross-sectional shape.

18. The method of claim 13, wherein the tip has a generally round cross-sectional shape.

19. The method of claim 18, wherein the tip further comprises a plurality of generally horizontal portions parallel to the proximal end to distal end direction of the tip forming generally planar rings around the circumference of the tip.

20. The method of claim 13, wherein the tip tapers towards the distal end.

21. The method of claim 20, wherein the tip includes a plurality of ridges converging towards the distal point.

22. The method according to claim 13, further comprising actuating the powered dental tool to impart energy in the form of vibrational movement, longitudinal reciprocating movement, rotational movement, reciprocating rotational movement, or a combination of the above movement schemes to the mounted tip.

23. A method of reducing periodontal pockets, the method comprising:
mounting a tip on a powered dental tool, the tip formed as an elongated member having a proximal end and a distal tip, the tip further comprising at least one gum tissue removal portion on the outer surface of the tip comprising a portion including features that remove gum tissue upon activation;
contacting the mounted tip against a patient's gum tissue to be removed;
actuating the powered dental tool to remove the patient's gum tissue including at least a portion of the patient's marginal gingiva extending apically in a generally linear direction to the base of the pocket such that enough soft tissue is removed to expose a previously subgingival tooth surface or dental implant surface sufficient to allow a clinician to visualize the tooth or dental implant surface; and
effecting powered debris removal of accretions from a tooth surface or dental implant surface with the tip during the same procedure as the gum tissue removal by contacting the tooth surface with the tip.

24. The method according to claim 23, wherein contacting the mounted tip against a patient's gum tissue to be removed comprises, inserting the distal end of the tip into a periodontal pocket and contacting a lining of the pocket with the tip and actuating the powered dental tool to remove the patient's gum tissue comprises removing gum tissue from the inside of the periodontal pocket.

25. The method of claim 23, further comprising redirecting water flow for cooling the powered dental tool from exiting the powered dental tool near the mounted tip to flush the operative site to exiting at another location away from the mounted tip to increase gum removal efficiency at the operative site by actuation of a valve as directed by a practitioner operating the powered dental tool.

26. The method of claim 23, wherein contacting the tooth surface with the tip comprises contacting the tooth surface with a portion of the tip constructed from a material having a hardness that is less than the hardness of the tooth surface.

27. The method according to claim 23, wherein actuating the powered dental tool comprises actuating the powered dental tool to impart energy in the form of vibrational movement, longitudinal reciprocating movement, rotational movement, reciprocating rotational movement, or a combination of the above movement schemes to the mounted tip.

28. A method of removing gum tissue to reduce a periodontal or peri-implant pocket, the method comprising:
    mounting a tip on a powered dental tool, the tip formed as an elongated member having a proximal end and a distal tip, the tip further comprising at least one gum tissue removal portion on the outer surface of the tip comprising a portion including features that remove gum tissue upon activation;
    contacting the mounted tip against a patient's gum tissue to be removed; and
    actuating the powered dental tool to remove the patient's gum tissue at a point of contact with the mounted tip; and
    removing gum tissue to achieve reduction of a periodontal or peri-implant pocket, wherein removing gum tissue comprises removing at least a portion of the marginal gingiva of the pocket such that a distance from a newly created gingival zenith to the patient's alveolar crest is less than the distance of the patient's original gingival zenith to the patient's alveolar bone crest; and
    effecting powered debris removal of accretions from a tooth surface or dental implant surface with the tip during the same procedure as the gum tissue removal by contacting the tooth surface with the tip.

29. The method according to claim 28, wherein contacting the mounted tip against a patient's gum tissue to be removed comprises, inserting the distal end of the mounted tip into a periodontal pocket or peri-implant pocket and contacting a lining of the pocket with the tip to remove the gum tissue from the inside of the pocket to create a visible gap between the patient's gum tissue and a tooth surface or a dental implant surface that allows a clinician to visualize subgingival structures for diagnosis or treatment.

30. The method of claim 28, further comprising redirecting at least a portion of water flow for cooling the powered dental tool from exiting the powered dental tool directed to the mounted tip to flush the operative site to exiting at another location away from the mounted tip and away from the operative site to increase gum removal efficiency.

31. The method according to claim 28, wherein actuating the powered dental tool comprises actuating the powered dental tool to impart energy in the form of vibrational movement, longitudinal reciprocating movement, rotational movement, reciprocating rotational movement, or a combination of the above movement schemes to the mounted tip.

32. A method of removing gum tissue, the method comprising:
    mounting a tip on a powered dental tool, the tip formed as an elongated member having a proximal end and a distal end, the tip further comprising at least one gum tissue removal portion on the outer surface of the tip comprising a portion including features that remove gum tissue upon activation;
    contacting the mounted tip against a patient's gum tissue to be removed comprising inserting the distal end of the mounted tip into a periodontal pocket;
    contacting a lining of the pocket with the tip; and
    actuating the powered dental tool to remove the gum tissue from the inside of the periodontal pocket, wherein removing gum tissue comprises removing at least a portion of the marginal gingiva of the pocket to reduce a distance from a newly created gingival zenith to the patient's alveolar crest.

33. The method of claim 32, further comprising contacting the tooth surface or dental implant surface with the tip to thereby remove accretions therefrom during the same procedure as the gum tissue removal.

34. The method of claim 33, wherein contacting the tooth surface with the tip comprises contacting the tooth surface with a portion of the tip constructed from a material having a hardness that is less than the hardness of the tooth surface.

35. The method of claim 32, further comprising redirecting at least a portion of water flow for cooling the powered dental tool from exiting the powered dental tool directed to the mounted tip to flush the operative site to exiting at another location away from the mounted tip and away from the operative site to increase gum removal efficiency.

36. The method of claim 32, wherein the tip has a triangular cross-sectional shape.

37. The method of claim 32, wherein the tip has a generally round cross-sectional shape.

38. The method of claim 37, wherein the tip further comprises a plurality of generally horizontal portions parallel to the proximal end to distal end direction of the tip forming generally planar rings around the circumference of the tip.

39. The method of claim 32, wherein the tip tapers towards the distal end.

40. The method of claim 39, wherein the tip includes a plurality of ridges converging towards the distal point.

41. The method according to claim 32, further wherein actuating the powered dental tool comprises actuating the powered dental tool to impart energy in the form of vibrational movement, longitudinal reciprocating movement, rotational movement, reciprocating rotational movement, or a combination of the above movement schemes to the mounted tip.

42. A method of removing gum tissue to reduce a periodontal pocket, the method comprising:
    mounting a tip on a powered dental tool, the tip formed as an elongated member having a proximal end and a distal end, the tip further comprising at least one gum tissue removal portion on the outer surface of the tip comprising a portion including features that remove gum tissue upon activation;
    contacting the mounted tip against a patient's gum tissue to be removed outside the periodontal pocket, wherein the patient's gum tissue to be removed includes an original gingival zenith adjacent the pocket; and
    actuating the powered dental tool to remove the gum tissue by removing at least a portion of the patient's gingival margin to reduce a distance from a newly created gingival zenith to the patient's alveolar crest as compared to the patient's original gingival zenith.

43. A tip for use in removing gum tissue with a powered dental tool, comprising:
   an elongated member having a proximal end and a distal end;
   a tool attachment structure for mounting to a tip mounting structure accessible at the proximal end, such that upon mounting to a powered tool the tip may be actuated by the application of energy through the powered tool; and
   at least one gum tissue removal portion on the outer surface of the tip that when brought in contact with a patient's gum tissue and actuated will remove gum tissue, and comprising a base portion near the proximal end; and
      a distal tapering portion comprising a plurality of portions defined by generally flat surfaces extending generally parallel to an axis defined by the proximal end to distal end direction of the tip and a plurality of generally planar portions extending in a direction orthogonal to the axis defined by the proximal end to distal end direction of the tip, with at least with at least two of the generally planar portions separated by portions defined by generally flat surfaces to define contiguous tiers receding stepwise towards the distal end of the tip.

44. The tip of claim 43, further comprising a first tapered portion extending from the distal end of the tip to the contiguous tiers.

45. The system of claim 43, wherein the working tip has a generally round cross-sectional shape.

46. The system of claim 45, wherein the contiguous tiers are generally flat ring-shaped portions.

* * * * *